United States Patent [19]

Iwanami et al.

[11] Patent Number: 5,008,118

[45] Date of Patent: Apr. 16, 1991

[54] METHOD FOR PRODUCING ORGANIC AGENT COATED WITH POWDERS OF COATING AGENT

[75] Inventors: Koichi Iwanami, Yokohama; Masatsugu Ito, Tokyo, both of Japan

[73] Assignee: Nippon Oil and Fats, Tokyo, Japan

[21] Appl. No.: 208,996

[22] Filed: Jun. 17, 1988

[30] Foreign Application Priority Data

Jun. 23, 1987 [JP] Japan ................ 62-154398

[51] Int. Cl.$^5$ ............................................. A61K 9/16
[52] U.S. Cl. .................................... 424/498; 424/476; 424/494; 424/497; 424/499; 424/450
[58] Field of Search ............... 424/498, 450, 476, 494, 424/497, 499

[56] References Cited

U.S. PATENT DOCUMENTS

| | | | |
|---|---|---|---|
| 2,828,206 | 3/1958 | Rosenberg | 424/498 |
| 2,921,883 | 1/1960 | Reese et al. | 424/498 X |
| 3,078,216 | 2/1963 | Greif | 424/498 |
| 3,119,742 | 1/1964 | Heimlich et al. | 424/498 |
| 3,867,556 | 2/1975 | Darragh et al. | 424/498 X |
| 4,797,288 | 1/1989 | Sharma et al. | 424/476 |

FOREIGN PATENT DOCUMENTS

| | | | |
|---|---|---|---|
| 0043254 | 1/1982 | European Pat. Off. | 424/498 |
| 0821790 | 10/1959 | United Kingdom | 424/498 |
| 1044572 | 10/1966 | United Kingdom | 424/498 |

Primary Examiner—Thurman K. Page
Attorney, Agent, or Firm—Darby & Darby

[57] ABSTRACT

A method for producing a coated organic agent is provided. The method comprises contacting a coating agent with core powders of an organic substance so that the coating agent collides against the core powders, and attaching the coating agent onto the overall surface of each of the core powders, whereby the core powders are coated by the coating agent. The coating agent contains at least lipid powders having a melting point not lower than 40° C.

14 Claims, No Drawings

METHOD FOR PRODUCING ORGANIC AGENT COATED WITH POWDERS OF COATING AGENT

BACKGROUND OF THE INVENTION

This invention relates to a method for producing a coated organic agent produced by coating core powders with powders of a coating agent. More particularly, it relates to a method for producing a coated organic agent that may be used as food additives, feed additives or so-called health foods.

The coated organic agents have been used in many applications in which the coating performance of these agents is of utmost importance. For example, when using the coated organic agent of organic acids or salts of organic acids in processed meat or fish paste, the properties of storage stability of the processed meat or fish paste may be improved by adjusting the pH of the products. However, when the organic acids and/or salts of organic acids are added directly, the physical properties of the products are impaired. When the organic acids or salts thereof are coated, it becomes possible to adjust the pH after heating the products. The organic acids liable to decomposition or oxidation on contact with water, such as L-ascorbic acid, may be improved in storage properties when coated and thus shut off from contact with air or moisture. In addition, when the organic acids and/or salts of the organic acids have foreign odor or otherwise affect the flavor of food products, coating gives rise to masking effects. When vitamins are directly used as additives for pisciculture, it may occur that thiamine (vitamin B ) is decomposed by thiaminase contained in fish, thus causing mortality of the fish in the farm due to thiamine deficiency. With other vitamins, the effect of the vitamin may be lost on account of environmental factors, such as moisture, ambient light, heat or pH. Also, when the vitamins are added to foods, it may occur that the odor and taste peculiar to the vitamins affect the taste or flavor of the foods. In these cases, the vitamins may be coated for masking effects When amino acids are directly used as feed additives for ruminating animals, it may occur that the amino acids be decomposed by the action of microorganisms in the first stomach or rumen of the animals.

In other applications of the amino acids, it may occur that the effect of amino acids may be lost on account of environmental factors, such as moisture, ambient light, heat or pH. Also, when the amino acids are added to foods, the taste or flavor of the foods may be affected by the odor or taste proper to the amino acids, as in the case of the vitamins. In order to prevent this, the amino acids may be coated for masking, effects.

There has been much research in developing the methods for producing the coated organic agents The methods employed at present may be classified into the following two categories. According to the first method, an organic substance is suspended in melted hardened oil or wax and the resulting suspension is sprayed by a sprayer or a rotary disk so as to be cooled and solidified to prepare a coated product. More concretely, for coating organic acids and/or salts of organic acids by this method, there are known a method for producing a coated organic acid as disclosed in Japanese Patent Publication No. 32217/1970 and a method for producing a coated organic acid as disclosed in Japanese Patent Publication No. 31476/1978. As the prior art product in which water-soluble vitamins are coated by this method, there are known a raw feed composition for pisciculture as described in Japanese Patent Publication No. 13192/1975 and a feed for pisciculture as described in Japanese Laid-Open Patent Publication No. 205461/1983. As the prior art product in which amino acids are coated by this method, there are known a feed additive through the first stomach or rumen of ruminating animals as described in Japanese Laid-Open Patent Publication No. 154956/1981, and a feed additive composition for ruminating animals, as described in Japanese Laid-Open Patent Publication No. 141242/1985. According to the second method, known as the fluidized layer process, an organic substance is floated under the force of a fluid flow from the lower side and the melted coating agent such as hardened oil or wax is sprayed from the upper side for coating the organic substance. For example, as a prior art method for coating water-soluble vitamins, there is known a method for coating a vitamin particulate material as described in Japanese Laid-Open Patent Publication No. 52221/1975 and, as a prior art product in which amino acids are coated by this method, there is known a particulate material for feed additives as described in Japanese Laid-Open Patent Publication No. 37054/1986.

However, sufficient coating cannot be accomplished in any of the above methods such that sufficient performance of the coated agents cannot be exhibited for the above-described applications.

In addition, because of the lower contents of the core organic substances, an increased amount of the coating organic agents needs to be used for practical applications, resulting in elevated manufacture costs.

Also, the coating agents need to be melted and sprayed or a fluidized layer needs to be formed with considerable energy consumption, while there are required troublesome operation and maintenance for such coating systems.

SUMMARY OF THE INVENTION

It is a principal object of the present invention to provide a method for producing a coated organic agent according to which the coating performance may be significantly improved and the organic substance may be effectively protected against other components or environmental factors including ambient light, heat, moisture or outside air.

It is another object of the present invention to provide a method for producing a coated organic agent according to which there is no necessity for melting the coating agent and hence larger energy consumption may be avoided while the maintenance operation of the coating system may be facilitated.

It is a further object of the present invention to provide a method for producing a coated organic agent according to which the content of the organic core substance may be increased and sufficient effect as the organic substance may be exhibited with the use of a smaller amount of the coating agent with resulting decrease in manufacture costs.

It is yet another object of the present invention to provide a coated organic agent that is stable under a neutral state and melted under an acidic state.

The above and other objects of the invention will become apparent from the following description.

According to the present invention, there is provided a method for producing a coated organic agent comprising contacting a coating agent with core powders of an organic substance so that the coating agent collides against the core powders, the coating agent containing at least lipid powders having a melting point not lower than 40° C. and attaching the coating agent onto the overall surface of each of the core powders, whereby the core powders are coated by the coating agent.

PREFERRED EMBODIMENTS OF THE INVENTION

The present invention will be explained in more detail.

The core powders of an organic substance employed in the present invention include organic substances selected from the group consisting of powders of organic acids, powders of salts of organic acids, powders of water-soluble vitamins and/or salts and/or esters thereof, powders of amino acids and/or salts and/or esters thereof and mixtures thereof and may be of crystalline or particulate form at ambient temperatures. The aforementioned powders of organic acids include those of sorbic acid, propionic acid, fumaric acid, maleic acid, dehydroacetic acid, benzoic acid, citric acid, malic acid, succinic acid, tartaric acid, oxalic acid, L-ascorbic acid, lactic acid, acetic acid, butyric acid, adipic acid, tannic acid, gallic acid, phytic acid, and mixtures thereof. The aforementioned salts of organic acids may be those found naturally or prepared upon synthesis and may include sodium, calcium, potassium, magnesium, iron, copper and zinc salts of the aforementioned organic acids, and mixtures thereof.

The aforementioned powders of the water-soluble vitamins may include, for example, vitamin $B_1$, vitamin $B_2$. vitamin $B_6$, vitamin $B_{12}$, vitamin $B_{13}$, vitamin $B_{14}$, vitamin $B_{15}$, lipoic acid, nicotinic acid, nicotinamide, pantothenic acid, folic acid, p-aminobenzoic acid, biotin, choline, inositol, vitamin L, vitamin U, vitamin C, vitamin P and mixtures thereof. A calcium, sodium, potassium, magnesium, iron, copper or zinc salt of the vitamins, salts such as hydrochlorate or nitrate and other derivatives of the aforementioned vitamins, such as esters of phosphoric, acetic, succinic, maleic or glutamic acid with the vitamins, may also be employed as the water-soluble vitamins. Water-soluble derivatives of oil-soluble vitamins, such as vitamin A, vitamin D, vitamin E or vitamin K, more concretely, vitamins rendered water-soluble by derivatives such as esters of phosphoric, acetic, succinic, maleic or glutamic acid with the vitamins, may also be employed. Examples of such water-soluble vitamin derivatives include menadion dimethyl hydrogen sulfite pyrimidinol and menadion sodium hydrogen sulfite. Mixtures of water-soluble vitamins obtained upon selectively combining two or more of the aforementioned compounds may also be used according to the usage and application.

As the powders of amino acids, $\alpha$-amino acids, $\beta$-amino acids, other amino acids or mixtures thereof, may be employed. The $\alpha$-amino acids may include, for example, monoamino monocarboxylic acids, such as DL-alanine, L-valine, leucine, L-isoleucine, L-phenylalanine, tyrosine, diiodetyrosine, DL-threonine, L-threonine, DL-tryptophane, L-tryptophane, serine, proline, hydroxyproline, thyroxine, DL-methionine, L-methionine, cystine or cysteine, monoamino dicarboxylic acids, such as aspartic acid, L-glutamic acid, asparagine or glutamine and diamino monocarboxylic acids such as D lysine, L-lysine, hydroxylysine, arginine or histidine. The $\beta$-amino acids may include, for example, $\beta$-alanine and $\beta$-aminobutyric acid. The other amino acids may include, for example, $\gamma$-aminobutyric acid, $\delta$-amino n-valeric acid and optical isomers of these amino acids. In addition, a calcium, sodium, potassium, magnesium, iron, copper or zinc salt, other salts such as hydrochrolates or nitrates of the aforementioned amino acids, derivatives such as esters of phosphoric acid or acetic acid and salts formed by two or more kinds of the aforementioned amino acids, may also be employed as the powders of amino acids.

The core powders of the aforementioned organic substance employed in the present invention may be pre-coated by a coating component. The coating component may include a water-soluble component, an oily component and a high polymeric component. More concretely, the water-soluble component may be enumerated for example by sugar, proteins, other amino acids and inorganic salts. The oily component may be enumerated for example by natural oils and fats, hardened oils, waxes, fatty acid monoglycerides, fatty acid diglycerides, fatty acids and other lipids. The high polymeric component may be enumerated for example by polyvinyl alcohol, carboxymethyl cellulose and polystyrene. Pre coating may be performed by any known methods, such as a method wherein the aforementioned organic substance is dispersed and suspended in the melted coating component and the resulting suspension is sprayed and allowed to cool, or a method known as the fluidized layer method wherein the coating component is sprayed onto the organic substance in the fluidized state.

According to the present invention, the lipid powders having a melting point not lower than 40° C. and at least contained in the coating agent for coating the overall surfaces of the core powders may include, for example naturally available animal and vegetable oils, such as beef tallow, hardened beef tallow fats, hardened fish oils, hardened soybean oil, hardened rapeseed oil, fatty acid monoglycerides, fatty acid diglycerides, propyleneglycol fatty acid esters, saccharose fatty acid esters, fatty acids, higher alcohols, waxes, phosphorus- or nitrogen-containing phospholipids, glycolipids containing sugar as the constituent, sulfolipids containing sulfonic acid groups, sterol, hydrogenation products thereof and mixtures thereof. The lipid powders having a melting point lower than 40° C. cannot be used because of the risk of possible melting during the preparation of the coated organic agent. However, the coating agent may contain lipids having a melting point lower than 40° C. if the coating agent as a whole has a melting point not lower than 40° C. As such coating agent, there may be mentioned a combination of waxes and coconut oil, a combination of completely hardened rapeseed oil and partially hardened rapeseed oil and a combination of fatty acids and soybean oil.

The aforementioned coating agent may additionally contain powders stable under a neutral state and melted under an acidic state. These powders stable under a neutral state and melted under an acidic state may include salts such as calcium carbonate, tricalcium phosphate, calcium hydrogen phosphate, trimagnesium phosphate, zinc phosphate, aluminum phosphate, calcium silicate, calcium pyrophosphate, magnesium carbonate, cobalt carbonate and lead carbonate, nitrogen-containing polysaccharides such as chitosan and chitin, metal salts of polysaccharides such as calcium alginate, cellulose derivatives such as benzylaminomethyl cellulose, dimethylaminomethyl cellulose, piperidylethylhydroxyethyl cellulose, cellulose acetate, and cellulose acetate diethylaminoacetate, and polyvinyl derivatives such as vinyldiethylamine-vinylacetate copolymer, polyvinylethylpyridine, polyvinyldiethylamino acetoacetal and polydimethylaminoethyl methacrylate. The total amount of the lipid powders and the powders stable under a neutral state and dissolved under an acidic state may be in the range of 5 to 80 wt. % based on the total weight of the coating agent in its entirety.

In the method for producing the coated organic agent of the present invention, the core powders of the organic substance or the pre coated core powders on the one hand and the coating agent containing the lipid powders having a melting point of not lower than 40° C. or further containing the powders stable under a neutral state and melted under an acidic state, on the other, are contacted with each other so that the coating agent collides against the core powders. Thus, using conventional mixers, ball mills, electric mortars, high-efficiency mixers for powders or devices for mixing and contacting the powders by high-speed air countercurrents, the powders are contacted with one another and with the inner walls and other portions of the devices such that only the surfaces of the core powders and/or the coating agent are effectively melted under the evolved friction heat for attaching and coating the coating agent on the overall surfaces of the core powders. It is desirable that such contact and collision be preferably effected at an r.p.m. of 500 to 8000 when the particle size of each of the core powders is less than 20 microns and at an r.p.m. of 5000 or lower when the particle size of each of the core powders is not less than 20 microns. When the r.p.m. is less than 500 for the particle size less than 20 microns, there are some cases where the core powders are not coated sufficiently. When the r.p.m. exceeds 8000 for the particle size less than 20 microns or when the r.p.m. exceeds 5000 for the particle size not less than 20 microns, there may be some cases where the core powders may be undesirably crushed to pieces with the powder contents flying off.

The contacting and colliding temperature may preferably be 10° C. or more lower than the melting point of the lipid powders at least contained in the coating agent. For example, when the melting point of the lipid powders contained in the coating agent is 60° C., the core powders can be coated satisfactorily when the contacting and collision is effected at a temperature lower than 50° C. The coating performance may be improved further by mixing the core powders and the coating agent in the powder state in advance of the contacting and collision.

The particle size of each of the core powders employed in the present invention may preferably be in the range between 1 micron and 1 mm, while each of the core powders may be spherical or of indefinite or irregular shape. The particle size ratio of each of the core powders to the coating agent (core powder particle size/coating agent particle size) is preferably 0.5 to 1000 and more preferably 10 to 200. Under conditions other than these specific conditions, it may occur that the coated organic agents are not produced satisfactorily.

The mixing ratio of the core powders and the coating agent (weight of the core powders/weight of the coating agent) may be selected to be within the range of 0.1 to 100. However, it is preferred that the mixing ratio be adjusted in connection with the particle size ratio. In case of a larger particle size ratio, a larger mixing ratio is preferably employed. In case of a lower particle size ratio, the mixing ratio is preferably selected to be not higher than 4. It cannot be said simply that the coating performance may be improved by using a lower mixing ratio. Thus, it may occur that higher coating performance may be achieved by using a higher mixing ratio. It will be noted that the coating performance may be additionally improved for the same mixing ratio when the coating agent is divided in two or more fractions and the attaching and coating operation is peformed two or more times using each fraction for each attaching and coating operation.

The coated organic agent produced in accordance with the method of the present invention is significantly improved in the coating performance thereof as compared with the conventional coated agents, such that influences from environmental factors such as ambient light, heat, moisture or outside air or contact with other components or ingredients may be inhibited positively, so that the effect proper to the various organic substances is not lost when the coated agent is used in foodstuff or in feed additives. In addition, when the powders stable under a neutral condition and melted under an acidic condition are contained in the coating agent for the preparation of the coated organic agent, the core organic substance may be effectively passed through the first stomach of the ruminating animal without being digested in the first stomach and released for digestion in the other stomachs.

It will be noted that, since the contents of the organic substance in the coating agent may be increased in accordance with the present invention, the amount of addition of the coating agent itself may be lowered with resulting reduction in costs involved in the preparation of the coating agent.

It will be noted further that the method for preparing the coated organic agent of the present invention may be simplified in operability as compared with the prior art methods with corresponding saving in energy consumption.

As described hereinabove, the coated organic agents of the present invention may have many merits not attainable in the prior art and may be used advantageously in, for example, the preparation of so-called health foods.

EXAMPLES OF THE INVENTION

The present invention will be explained further upon reference to Examples and Comparative Examples. Incidentally, percentages represent % by weight.

COMPARATIVE EXAMPLE 1

250 g of L-ascorbic acid having a mean particle size of 80 microns (graded or classified goods manufactured by Daiich Seiyaku Company Limited) was added to 1 kg of melted hardened rapeseed oil having a melting point of 63.4° C. (manufactured by Nippon Oil and Fats Co. Ltd.) and dispersed sufficiently by a homogenizing mixer. The resulting mixture was sprayed by a rotary disk type sprayer into a chamber maintained at 30° C. to produce a powdered product.

COMPARATIVE EXAMPLE 2

1 kg of potassium sorbate with a mean particle size of 50 microns was added to 2.5 kg of a melted rice wax having a melting point of 79.4° C. and dispersed thoroughly by a homogenizing mixer. The operation was performed in the same way as in the Comparativer Example 1 to produce a powdered product having a mean particle size in the range from 50 to 300 microns.

EXAMPLE 1

35 g of fumaric acid having a mean particle size of 200 microns and 15 g of monoglyceride stearate were charged into a centrifugal rotating type mixer manufactured by Okada Seiko KK under the trade name of Mechanomill-MM 10 along with ten bronze balls and mixed at 25° C. for two hours at the r.p.m. of 500. 0.5 g of the produced powders and 100 ml of ethanol were charged into a triangular flask and shaken in a constant temperature shaker at a rate of 100 times per minute and the amount of fumaric acid eluated in ethanol was estimated by alkaline titration. The results of the shaking time and the rate of elution are shown in Table 1, wherein the rate of eluation stands for the rate in percentage of the eluated fumaric acid to the total fumaric acid.

TABLE 1

| Shaking Time (minutes) | 20 | 40 | 60 |
|---|---|---|---|
| Rate of Elution (percent) | 30.6 | 49.8 | 64.1 |

It will be seen from above that the rate of elution of fumaric acid is significantly lowed upon carrying out the operation of the present invention. A similar operation carried out without coating in accordance with the present invenion has revealed that the rate of elution reached 100 percent soon after shaking.

A test for practical application was conducted using the coated fumaric acid. 1500 g of frozen minced meat of Alaska pollack, 224 g of condiments such as table salt and sugar, 100 g of starch, 1200 g of water and coated fumaric acid containing 0.2% of pure fumaric acid, were mixed thoroughly to produce a minced meat for fish cake, which was then boiled to produce the fish cake. The product showed good resiliency and preservative properties such that it could be preserved at 30° C. for five days, whereas the product not admixed with fumaric acid could be preserved at 30° C. for 1.5 days.

EXAMPLE 2

40 g of L-ascorbic acid with mean particle size of 150 microns and 10 g of hardened rapeseed oil with a mean particle size of 10 microns and a melting point of 63.4° C. (manufactured by Nippon Oil and Fats Co. Ltd.) were charged into a centrifugal rotatory type mixer manufactured by Okada Seiko KK under the trade name of Mechanomill-MM10, along with ten bronze balls, and mixed together at 25° C. for three hours at the r.p.m. of 300.

Elution tests were conducted on the produced powders (contents of L-ascorbic acid, 80%) and the powders produced in the Comparative Example 1 (contents of L-ascorbic acid, 50%). In these tests, an elution tester manufactured by Toyama Sangyo KK was employed, and 0.024 g of L-ascorbic acid (pure contant) was added to 800 g of water. The rate of elution was found from the measured values of light absorptivity at 270 nm. The results are shown in Table 2.

TABLE 2

| | 10 min | 20 min | Time Elapsed Until Completion of Elution |
|---|---|---|---|
| Ex. 2 | 38.4 | 66.2 | 94 min |
| Comp. Ex. 1 | 96.7 | 99.7 | 22 min |

In the above table, the values for 10 and 20 minutes represent the rates of elution (%).

It will be seen from the above results that the product according to the present invention has higher L-ascorbic acid contents while exhibiting good coating performance.

EXAMPLE 3

900 g of the powders obtained in Comparative Example 2 and 100 g of fine powders of rice wax having a mean particle size of 17 microns and a melting point of 79.4° C., were mixed in the powder form and then mixed at the r.p.m. of 3000 using a mixer manufactured by Nara Machinary Co., Ltd. under the trade name of Nara Hybridization System. The temperature of the powders at the completion of the mixing was 53° C. Elution tests were conducted on the produced powders and the powders produced in accordance with Comparative Example 2. The results are shown in the following Table 3, wherein the rate of elution was found from the light absorptivity at 255 nm.

TABLE 3

| | 10 min | 20 min | Time Elapsed Until Complete Elution |
|---|---|---|---|
| Ex. 3 | 26.9 | 60.1 | 116 min |
| Comp. Ex. 2 | 91.4 | 98.2 | 28 min |

The values for 10 and 20 minutes in the Table represents the rates of elution (%).

It is seen from the above results that the performance of the core powders coated only insufficiently by precoating is improved significantly when additionally coated in accordance with the present invention.

COMPARATIVE EXAMPLE 3

400 g of thiamine nitrate having a mean particle size of 124 microns was added to 2 kg of melted hardened rapeseed oil having a melting point of 64.1° C., manufactured by Nippon Oil and Fats Co. Ltd., and dispersed thoroughly in a homogenizing mixer. The resulting mixture was sprayed by a rotary disk type sprayer into a chamber maintained at 30° C. to produce a powdered product.

COMPARATIVE EXAMPLE 4

800 g of nicotinic acid having a mean particle size of 114 microns was added to 1.2 kg of melted carnauba wax having a melting point of 83.7° C. and dispersed thoroughly by a homogenizing mixer. The ensuing operation was performed in the same way as in Comparative Example 3 to produce a powdered product.

COMPARATIVE EXAMPLE 5

600 g of riboflavin having a mean particle size of 146 microns was added to 1.2 kg of melted monoglyceride stearate having a melting point of 64.7° C. and dispersed thoroughly by a homogenizing mixer. The ensuing operation was performed in the same way as in Comparative Example 3 to produce a powdered product having a particle size of 80 to 250 microns.

EXAMPLE 4

42 g of thiamine nitrate having a particle size of 24 microns and 18 g of hardened rapeseed oil having a mean particle size of 8.6 microns and a melting point of 64.1° C. (manufactured by Nippon Oil and Fats Co.

Ltd.) were charged into a centrifugal rotatory mixer manufactured by Okada Seiko KK under the trade name of Mechanomill-MM10, along with ten bronze balls, and mixed together at 25° C. for four hours at 300 r.p.m. The produced powders and the powders obtained in Comparative Example 3 were added to minced anchovy so that the amount of thiamine nitrate in the mixture is equal to 10 mg/100 g, and the rate of thiamine decomposition with lapse of time was checked. The amount of thiamine was measured by adding a cyanogen bromide reagent to an extraction liquid and measuring light absorptivity at the wavelength of 368 nm in accordance with the Japanese Pharmacopeia.

The results are shown in Table 4.

TABLE 4

| Time Elapsed | Ex. 4 | Comp. Ex. 3 | Non-coated Products |
|---|---|---|---|
| 0 hr. | 100% | 100% | 100% |
| 2 hrs. | 95.4 | 83.1 | 12.6 |
| 5 hrs. | 86.9 | 57.8 | 3.7 |
| 10 hrs. | 67.6 | 30.2 | 0.7 |
| 16 hrs. | 50.1 | 18.5 | 0 |
| 24 hrs. | 40.4 | 13.0 | 0 |

It is seen from above that the rate of decomposition of thiamine nitrate is significantly lowered upon carrying out the operation of the present invention.

EXAMPLE 5

160 g of nicotinic acid having a mean particle size of 114 microns and 40 g of carnauba wax having a mean particle size of 8 microns and a melting point of 83.7° C. available as a crushed product from Nippon Oil and Fats Co., Ltd. were mixed together in the powder form and then mixed at the r.p.m. of 3500 in a mixer manufactured by Nara Machinary Co., Ltd. under the trade name of Nara Hybridization System. The temperature of the powders after mixing was 55° C. The produced powders having the nicotinic acid content of 80% and the powders produced in Comparative Example 4 with the nicotinic acid content of 40% were put to elution tests in which an amount of the produced powders equivalent to 0.3 g of nicotinic acid and 50 ml of water were charged each time into a triangular shaped flask and shaken by a constant temperature shaker at a rate of 100 times a minute and the amount of nicotinic acid eluated in the water layer was estimated by titration with a solution of sodium hydroxide. The results of the shaking time and the rate of elution are shown in Table 5, in which the rate of elution represents the rate in percentage of eluated nicotinic acid to the total nicotinic acid.

TABLE 5

| Shaking Time (minutes) | | 20 | 40 | 60 |
|---|---|---|---|---|
| Rate of Elution (%) | Ex. 5 | 27.4 | 42.2 | 63.7 |
| | Comp. Ex. 4 | 47.1 | 76.5 | 96.8 |

It is seen from the above results that the product having high nicotinic acid contents and good coating performance is obtained in accordance with the present invention.

EXAMPLE 6

45 g of the powders produced in Comparative Example 5 and 5 g of fine powders of monoglyceride stearate having a mean particle size of 17 microns and a melting point of 64.7° C. available as a crushed product from Nippon Oil and Fats Co., Ltd. were charged into a centrifugal rotatory type mixer manufactured by Okada Seiko KK under the trade name of Mechanomill-MM 10, along with 15 bronze balls, and processed at 25° C. for two hours at 500 r.p.m. The produced powders and the powders in Comparative Example 5 were put to elution tests using an automatic elution test system manufactured by Toyama Sangyo KK. The tests were conducted using a phosphoric acid buffer solution of pH 7 as an elution liquid and at a wavelength of 265 nm The results are shown in Table 6.

TABLE 6

| | 10 minutes | 20 minutes | Time Elapsed Until Complete Elution |
|---|---|---|---|
| Ex. 6 | 34.1 | 66.5 | 102 minutes |
| Comp. Ex. 5 | 88.4 | 98.8 | 25 minutes |

The values in the Table for 10 and 20 minutes represent the rates of elution (%).

It is seen from the above results that the performance of the water-soluble vitamins coated only insufficiently by pre-coating is improved significantly when additionally coated in accordance with the present invention.

COMPARATIVE EXAMPLE 6

400 g of L-lysine hydrochlorate having a mean particle size of 112 microns were added to 1.9 kg of melted hardened soybean oil powders having a melting point of 60.7° C. and dispersed sufficiently in a homogenizing mixer. The mixture was sprayed by a rotary disk type sprayer into a chamber maintained at 30° C. to produce a powdered product. The content in the product of L-lysine hydrochlorate was 20%.

COMPARATIVE EXAMPLE 7

1 kg of DL-methionine having a mean particle size of 67.4 microns, 100 g of calcium carbonate and 100 g of calcium alginate were added to 1 kg of melted rice wax having a melting point of 81.1° C. and dispersed thoroughly by a homogenizing mixer. The ensuing operation was performed in the same way as in Comparative Example 6 to produce a powdered product with DL-methionine contents of 45.5%.

COMPARATIVE EXAMPLE 8

600 g of L-sodium glutaminate having a mean particle size of 216 microns was added to a melted mixture of 1.2 kg of hardened rapeseed oil having a melting point of 66.7° C. and 800 g of monoglyceride stearate having a melting point of 64.4° C., and dispersed thoroughly by a homogenizing mixer. The ensuing operation was performed in the same way as in Comparative Example 6 to produce a powdered product having a particle size of 90 to 280 microns.

EXAMPLE 7

42 g of L-lysine hydrochrolate employed in Comparative Example 6 and 18 g of hardened soybean oil powders having a mean particle size of 9.4 microns were preliminarily mixed together and charged into a centrifugal rotatory type mixer manufactured by Okada Seiko KK under the trade name of Mechanomill MM 10 along with 10 bronze balls. The mixture was processed at 25° C. at 300 r.p.m. for three hours to produce coated amino acid with L-lysine hydrochlorate contents of 70%.

EXAMPLE 8

42 g of L-lysine hydrochlorate employed in Comparative Example 6 and 9 g of hardened soybean oil powders with mean particle size of 9.4 microns were preliminarily mixed and charged in a centrifugal rotatory type mixer manufactured by Okada Seiko KK under the trade name of Mechanomill- MM 10, along with ten bronze balls, where the mixture was processed at 25° C. for three hours at the r.p.m. of 300. Into the mixture were further added 9 g of hardened soybean oil powders and the resulting mixture was processed for three hours to produce coated amino acids with L-lysine hydrochlorate contents of 70%.

Table 7 shows the results of elution tests in water for Examples 7 and 8 and Comparative Example 6. In these elution tests, an amount of the produced powders equivalent to 2 g of L-lysine hydrochlorate and 50 ml of water were charged into a triangular flask and shaken by a shaker at 37° C. at a rate of 100 times per minute and the amount of L-lysine hydrochlorate eluated in 5 ml of a water layer was determined by perhydrochloric acid titration. The rate of elution represents the rate in percentage of the eluated amount of L-lysine hydrochlorate to the total amount of L-lysine hydrochlorate.

TABLE 7

|  | EX. 7 | EX. 8 | Comp. Ex. 6 |
| --- | --- | --- | --- |
| 15 minutes | 15.2 | 8.1 | 73.3 |
| 30 minutes | 24.5 | 14.8 | 94.6 |
| 60 minutes | 39.7 | 28.4 | 98.3 |
| 120 minutes | 50.6 | 40.2 | 100.0 |
| 150 minutes | 66.1 | 51.5 | 100.0 |
| 180 minutes | 76.2 | 57.4 | 100.0 |

It is seen from above that a product with high L-lysine hydrochlorate contents and good coating performance is obtained upon carrying out the operation in accordance with the present invention.

EXAMPLE 9

320 g of DL-methionine employed in Comparative Example 7, 64 g of rice wax powders with a mean particle size of 8.3 microns, 10 g of calcium carbonate having a mean particle size of 3.6 microns and 6 g of calcium alginate having a mean particle size of 17.4 microns were mixed and processed at 4000 r.p.m. for two minutes using a mixer manufactured by Nara Machinary Co., Ltd. under the trade name of Nara Hybridization System. The temperature of the powders after mixing was 55° C. The produced powders having DL-methionine contents of 80% and the powders produced in the Comparative Example 7 and having DL-methionine contents of 40% were put to elution tests. In these tests, a 0.1M sodium phosphate buffer solution and a 0.1 N hydrochloric acid were employed as the eluating solution for the artificial first stomach and as the gastric juice for the artificial fourth stomach, respectively. An amount of the produced powders equivalent to 3 g of DL methionine and 50 ml of water were charged in a triangular flask and shaken with a shaker at 37° C. at a rate of 100 times per minute and the amount of DL methionine eluated in a water layer was estimated by iodometry. The shaking was continued for 12 hours for the artificial first gastric juice and for 4 hours for the artificial fourth gastric juice, respectively. The results as well as the results for the Comparative Example 7 are shown in Table 8. The rate of elution represents the rate in percentage of eluated DL-methione to the total Dl-methionine.

TABLE 8

| Elution Liquid |  | (i) | (ii) |
| --- | --- | --- | --- |
| Rate of Elution (%) | Ex. 9 | 3.2 | 92.7 |
|  | Comp. Ex. 7 | 51.6 | 73.3 |

It is seen from the above results that the agent with high DL-methionine contents and superior selective elution properties is produced by the method of the present invention.

EXAMPLE 10

45 g of the powders produced in the Comparative Example 8 and 5 g of hardened rapeseed oil powders with a mean particle size of 6.6 microns and a melting point of 66.7° C. were charged into a centrifugal rotatory type mixer manufactured by Okada Seiko KK under the trade name of Mechanomill-MM 10, along with 15 bronze balls, and processed at 25° C. at 500 r.p.m. for two hours. The produced powders and the powders of the Comparative Example 8 were put to elution tests. A phosphric acid buffer solution, pH 7, was used as the elution liquid and a differential refractometer was used for detection. The results of the rate of elution are shown in Table 9. The rate of elution represents the rate in percentage of the eluated L-sodium glutaminate to the total L-sodium glutaminate.

TABLE 9

| Rate of Elution | 30 min. | 60 min. | 90 min. | 120 min. |
| --- | --- | --- | --- | --- |
| EX. 10 | 32.1 | 58.3 | 76.2 | 89.6 |
| Comp. Ex. 8 | 88.4 | 98.8 | 100.0 | 100.0 |

It is seen from the above results that the performance of amino acid coated only insufficiently by pre-coating is significantly improved when processed in accordance with the present invention.

Although the present invention has been described with reference to the specific examples, it should be understood that various modifications and variations can be easily made by those skilled in the art without departing from the spirit of the invention. Accordingly, the foregoing disclosure should be interpreted as illustrative only and not to be interpreted in a limiting sense. The present invention is limited only by the scope of the following claims.

What is claimed is:

1. A method for producing a coated organic agent comprising contacting a coating agent with core powders of an organic substance at a temperature less than the melting temperature of either the coating agent or core powder, so that said coating agent collides against said core powders with sufficient resultant frictional heating to cause adhesive binding of the coating agent of the core powder, said coating agent containing at least lipid powders having a melting point not lower than 40° C., and attaching said coating agent onto the overall surface of each of said core powders, whereby said core powders are coated by said coating agent, wherein said core powders of said organic substance are selected from the group consisting of powders of organic acids, powders of salts of organic acids, powders of water-soluble vitamins and/or salts and/or esters thereof, powders of amino acids and/or salts and/or esters thereof and mixtures thereof, wherein said organic acids are selected from the group consisting of sorbic acid, propionic acid, fumaric acid, maleic acid, dehydroacetic acid, benzoic acid, citric acid, malic acid, succinic acid, tartaric acid, oxalic acid, L-ascorbic acid, lactic acid, acetic acid, butyric acid, adipic acid, tannic acid, gallic acid, phytic acid and mixtures thereof, wherein said salts of organic acids are selected from the group consisting of sodium, calcium potassium, magnesium, iron, copper and zinc salts and mixtures thereof of organic acids selected from the group consisting of sorbic acid, propionic acid, fumaric acid, maleic acid, dehydroacetic acid, benzoic acid, citric acid, malic acid, succinic acid, tartaric acid, oxalic acid, L-ascorbic acid, lactic acid, acetic acid, butyric acid, adipic acid, tannic acid, gallic acid, phytic acid and mixtures thereof, wherein said water-soluble vitamins and/or salts and/or esters thereof are selected from the group consisting of vitamin $B_1$, vitamin $B_2$, vitamin $B_6$, vitamin $B_{12}$, vitamin $B_{13}$, vitamin $B_{14}$, vitamin $B_{15}$, lipoic acid, nicotinic acid, nicotinamide, pantothenic acid, folic acid, p-aminobenzoic acid, biotin, choline, inositol, vitamin L, vitamin U, vitamin C, vitamin P, calcium salts of said vitamins, sodium salts of said vitamins, potassium salts of said vitamins, magnesium salts of said vitamins, iron salts of said vitamins, copper salts of said vitamins, zinc salts of said vitamins, hydrochlorates of said vitamins, nitrates of said vitamins, esters of phosphoric acid with said vitamins, esters of acetic acid with said vitamins, esters of succinic acid with said vitamins, esters of maleic acid with said vitamins, esters of glutamic acid with said vitamins, and mixtures thereof, wherein said esters of said water-soluble vitamins are selected from the group consisting of esters of phosphoric acid, acetic acid, succinic acid, maleic acid and glutamic acid and mixtures thereof of oil-soluble vitamins selected from the group consisting of vitamin A, vitamin D, vitamin E, vitamin K and mixtures thereof, and wherein said amino acids and/or salts and/or esters thereof are selected from the group consisting of DL-alanine, L-valine, leucine, L-isoleucine, L-phenylalanine, tyrosine, diiodetyrosine, DL-threonine, L-threonine, DL-tryptophan, L-tryptophan, serine, proline, hydroxyproline, thyroxine, DL-methionine, L-methionine, cystine, cysteine, aspartic acid, L-glutamic acid, asparagine, glutamine, D-lysine, L-lysine, hydroxylysine, arginine, histidine, β-alanine, β-aminobutyric acid, γ-aminobutyric acid, δ-amino-n-valeric acid, calcium salts of said amino acids, sodium salts of said amino acids, potassium salts of said amino acids, magnesium salts of said amino acids, iron salts of said amino acids, copper salts of said amino acids, zinc salts of said amino acids, hydrochlorates of said amino acids, nitrates of said amino acids, esters of phosphoric acid with said amino acids, esters of acetic acid with said amino acids, and mixtures thereof.

2. The method according to claim 1 wherein said core powders of said organic substance are pre-coated by a coating component, wherein said coating component is selected from the group consisting of a water-soluble component, an oily component and a high polymeric component, wherein said water-soluble component is selected from the group consisting of sugar, proteins, inorganic salts, and mixtures thereof, wherein said oily component is selected from the group consisting of hardened oils, waxes, fatty acid monoglycerides, fatty acid diglycerides and mixtures thereof, and wherein said high polymeric component is selected from the group consisting of polyvinyl alcohol, carboxymethyl cellulose, polystyrene and mixtures thereof.

3. The method according to claim 2 wherein said core powders are pre-coated by dispersing said organic substance in the melted coating component to produce a suspension and spraying and cooling said suspension for coating said component on said organic substance.

4. The method according to claim 2 wherein said core powders are pre-coated by spraying said coating component onto the fluidized organic substance for coating said coating component on said organic substance.

5. The method according to claim 1 wherein said lipid powders are selected from the group consisting of beef tallow, hardened beef tallow fats, hardened fish oils, hardened soybean oil, hardened rapeseed oil, fatty acid monoglycerides, fatty acid diglycerides, propyleneglycol fatty acid esters, saccharose fatty acid esters, higher alcohols, waxes, phospholipids, sulfolipids, sterol, hydrogenation products thereof, and mixtures thereof 6. The method according to claim 1 wherein said coating agent further contains powders stable under a neutral state and melted under an acidic state.

7. The method according to claim 6 wherein said powders stable under the neutral state and melted under the acidic state are selected from the group consisting of calcium carbonate, tricalcium phosphate, calcium hydrogen sulfate, trimagnesium phosphate, zinc phosphate, aluminum phosphate, calcium silicate, calcium pyrophosphate, magnesium carbonate, cobalt carbonate, lead carbonate, chitosan, chitin, calcium alginate, benzylaminomethyl cellulose, dimethylaminomethyl cellulose, piperidylethylhydroxyethyl cellulose, cellulose acetate, cellulose acetate diethylamino acetate, vinyldiethylamine-vinyl acetate copolymer, polyvinylethyl pyridine, polyvinyldiethylamino acetoacetal, polydimethylaminoethyl methacrylate, and mixtures thereof.

8. The method according to claim 1 wherein a particle size of each of said core powders ranges between 1 micron and 1 mm and wherein a particle size ratio of each of said core powders to said coating agent (core powder particle size/coating agent particle size) ranges from 0.5 to 1000.

9. The method according to claim 1 wherein a mixing ratio of said core powders to said coating agent (weight of said core powders/weight of said coating agent) ranges from 0.1 to 100.

10. The method according to claim 1, wherein said coating agent is contacted with said core powders at a temperature lower than 10° C. or more than the melting point of said lipid powders.

11. The method according to claim 1 wherein said core powders having a particle size less than 20 microns are contacted with said coating agent at an r.p.m. of 500 to 8000.

12. The method according to claim 1 wherein said core powders having a particle size not less than 20 microns are contacted with said coating agent at an r.p.m. of 5000 or lower.

13. The method according to claim 1 wherein said coating agent is divided in two or more fractions and attached to and coated on said core powders in two or more times.

14. The method according to claim 1 wherein said coating agent contains lipids having a melting point lower than 40° C. and wherein said coating agent has a melting point not lower than 40° C.

* * * * *